(12) United States Patent
Heller

(10) Patent No.: US 8,728,526 B2
(45) Date of Patent: May 20, 2014

(54) COACERVATE MICROPARTICLES USEFUL FOR THE SUSTAINED RELEASE ADMINISTRATION OF THERAPEUTIC AGENTS

(75) Inventor: Phillip F. Heller, Baltimore, MD (US)

(73) Assignee: The United States of America, Represented by Secretary of Department of Health and Human Services, NIH, Washington, DC (US)

( * ) Notice: Subject to any disclaimer, the term of this patent is extended or adjusted under 35 U.S.C. 154(b) by 1883 days.

(21) Appl. No.: 11/659,976

(22) PCT Filed: Jul. 25, 2005

(86) PCT No.: PCT/US2005/026257
§ 371 (c)(1),
(2), (4) Date: Aug. 27, 2007

(87) PCT Pub. No.: WO2006/023207
PCT Pub. Date: Mar. 2, 2006

(65) Prior Publication Data
US 2008/0075778 A1 Mar. 27, 2008

Related U.S. Application Data

(60) Provisional application No. 60/602,651, filed on Aug. 19, 2004.

(51) Int. Cl.
*A61K 9/14* (2006.01)

(52) U.S. Cl.
USPC .............. 424/489; 530/300; 530/350; 514/2

(58) Field of Classification Search
None
See application file for complete search history.

(56) References Cited

U.S. PATENT DOCUMENTS

| 5,759,582 | A | 6/1998 | Leong et al. |
| 5,972,707 | A | 10/1999 | Roy et al. |
| 6,207,195 | B1 | 3/2001 | Walsh et al. |
| 6,410,517 | B1 | 6/2002 | Truong et al. |
| 6,475,995 | B1 | 11/2002 | Roy et al. |
| 7,534,449 | B2 * | 5/2009 | Saltzman et al. ............. 424/417 |
| 2004/0018228 | A1 | 1/2004 | Fischell et al. |

FOREIGN PATENT DOCUMENTS

WO WO 99/36089 7/1999
WO WO 2004/045647 6/2004

OTHER PUBLICATIONS

Vinogradov et al., "Nanogels for oligonucleotide delivery to the brain", Bioconjug Chem. 15(1): 50-60 Jan.-Feb. 2004.*
Truong,Vu L., et al.,"Targeted Delivery of Immunomicrospheres in Vivo",Journal of Delivery and Targeting of Therapeutic Agents,1995,166-174,vol. 2(3-4), Academic Press Inc.,US.
Shao,Wen, et al.,"Microcapsules obtained from complex coacervation of collagen and chondroitin sulfate",Journal of Biomaterials Science Polymer Edition, 1995,389-399,vol. 7(5), VSP, U.S.A.
Hanes, Justin, et al.,"Controlled Local Delivery of Inerleukin-2 by Biodegradable Polymers Protects Animals from Experimental Brain Tumors and Liver Tumors",Jul. 2001,899-906,vol . 18 (7), Plenum Publishing Corporation, New York, U.S.A.
Golumbek, Paul T., et al.,"Controlled Release, Biodegradable Cytokine Depots: A New Approach in Cancer Vaccine Design",American Association for Cancer Research, Dec. 1993,5841-5844 , vol . 53(24), Johns Hopkins Univ., Baltimore, U.S.A.
Chen, Yan, et al.,"Chitosan-dextran nanoparticles for delivery of an anti-angiogenisis peptide",Letters in Peptide Science,2003,621-629,vo1.10(5-6),Kluwer Academic Publishers, The Netherlands.

* cited by examiner

*Primary Examiner* — Anand Desai
(74) *Attorney, Agent, or Firm* — Swanson & Bratschun, L.L.C.

(57) ABSTRACT

The present invention relates to novel microparticles formed using a coacervation process, methods of forming the microparticles, and methods of using the microparticles for the sustained release administration of therapeutic agents.

6 Claims, No Drawings

COACERVATE MICROPARTICLES USEFUL FOR THE SUSTAINED RELEASE ADMINISTRATION OF THERAPEUTIC AGENTS

CROSS-REFERENCE TO RELATED APPLICATIONS

This application is the national stage application of International Application No. PCT/US2005/026257 under 35 U.S.C. §371, International Publication No. WO 2006/023207, and international filing date of 25 Jul. 2005, which claims priority to U.S. Patent Application Ser. No. 60/602,651, filed Aug. 19, 2004, which applications are hereby incorporated by reference in their entireties and to which priority is claimed.

STATEMENT OF GOVERNMENTAL INTEREST

This invention was funded by the National Institute on Aging at the National Institutes of Health. The United States Government has certain rights to this invention.

FIELD OF THE INVENTION

The present invention relates to novel microparticles formed using a coacervation process, methods of forming such microparticles, and methods of using such microparticles for the sustained release administration of therapeutic agents.

BACKGROUND OF THE INVENTION

Polymer matrix-based sustained-release formulations have gained significant interest in recent years for both parenteral and delivery of small molecules as well as proteins and other biological molecules. These delivery systems offer numerous advantages compared to conventional dosage forms, which include improved efficacy, reduced toxicity, convenience and improved patient compliance. Additionally, colloidal carriers such as microparticles are regarded as providing a promising approach for targeting drugs to specific organs that could permit the sustained release at the target site and reduce potential side effects.

Microparticles of the matrix type that are formed by the process of coacervation are desirable since they permit therapeutic agents to become incorporated into the microparticles under mild conditions. For example, the use of biocompatible and biodegradable anionic and cationic polymers in a coacervation process to form microparticles that incorporate a therapeutic agent has been described by Leong et al. (U.S. Pat. No. 5,759,582) and Walsh et al. (U.S. Pat. No. 6,207,195). Additionally, coacervate microparticles for the delivery of nucleic acids have been described by Roy et al. (U.S. Pat. Nos. 5,972,707 and 6,475,995) and Truong et al. (U.S. Pat. No. 6,410,517).

Coacervate microparticles that can be standardized and employed for the delivery of a variety of therapeutic agents are needed to enhance the efficiency of the formulation process for microparticle sustained release compositions. The invention described herein is directed to address this and other needs.

SUMMARY OF THE INVENTION

In one aspect, the invention relates to the recognition that binding components can be incorporated throughout the matrix of coacervate microparticles during the coacervation process and that therapeutic agents can be incorporated into the microparticles via a binding interaction, either directly or indirectly, between the binding component and the therapeutic agent.

In one aspect, the invention relates to a composition comprising microparticles having a matrix structure, wherein the matrix structure comprises the reaction product of at least one cationic polymer, at least one anionic polymer, and a binding component, and wherein the binding component is distributed throughout the matrix structure of the microparticle.

In one aspect, the invention relates to a composition comprising microparticles having a matrix structure, wherein the matrix structure comprises the reaction product of at least one cationic polymer, at least one anionic polymer, and a binding component, wherein the binding component is distributed throughout the matrix structure of the microparticle, wherein the binding component is one member of a specific binding pair comprising the binding component and a linking moiety, wherein the linking moiety is suitable for linkage with a variety of therapeutic agents, and wherein a therapeutic agent is linked to the linking moiety and is bound to the microparticles through the specific interaction of the linking moiety with the binding component.

In another aspect, the invention relates to a composition comprising microparticles having a matrix structure, wherein the matrix structure comprises the reaction product of at least one cationic polymer having a binding component covalently attached thereto and at least one anionic polymer, wherein the binding component is distributed throughout the matrix structure of the microparticle.

In another aspect, the invention relates to a composition comprising microparticles having a matrix structure, wherein the matrix structure comprises the reaction product of at least one cationic polymer and at least one anionic polymer having a binding component attached thereto, wherein the binding component is distributed throughout the matrix structure of the microparticle.

In another aspect, the invention relates to a method of forming microparticles having a matrix like structure comprising the steps of:

(a) forming microparticles by coacervation of at least one cationic polymer, at least one anionic polymer, and a binding component;

(b) stabilizing the microparticles by exposing the microparticles to a cross-linking agent under conditions suitable to cross-link the microparticles.

In another aspect, the invention relates to a method of administering a sustained release formulation of a therapeutic agent to a subject comprising administering to the subject a composition comprising microparticles having a matrix structure, wherein the matrix structure comprises the reaction product of at least one cationic polymer, at least one anionic polymer, and a binding component, wherein the binding component is distributed throughout the matrix structure of the microparticle, and wherein the therapeutic agent is bound to the binding component.

DESCRIPTION OF THE PREFERRED EMBODIMENTS

In one aspect, the invention relates to the recognition that the incorporation of a specific binding component in a matrix of microparticles formed by the process of coacervation. The use of such microparticles allows for the efficient manufacture and use of a wide variety of therapeutic agents in sustained release formulations.

In a preferred embodiment, the methods of the present invention involve the use of microparticles that are formed through the coacervation of at least one cationic polymer and at least one anionic polymer to form microparticles having a matrix like structure. Because this process depends on the interaction of a positively charged cationic polymer(s) and a negatively charged anionic polymer(s), the process is typically a "complex" coacervation process. However, under certain conditions and selections of cationic polymer and anionic polymer, certain agents may be used to promote the formation of a coacervate by inducing a; phase transition. Therefore, the process could also be considered a "simple" coacervation process under certain conditions. For example, certain agents such as sodium sulfate or ethanol may be used to promote a phase transition.

As used herein, the term "microparticles" is meant to encompass particles having an average mean diameter of micrometer size or of nanometer size. The size of the microparticles may be optimized for a particular application.

Cationic polymers and anionic polymers are used in the coacervation process of the invention. By "cationic polymer" or "anionic polymer," as used herein, is meant a polymer having a net positive charge or a net negative charge, respectively, under the conditions of coacervation. In one embodiment of the invention, the cationic and anionic polymers are different polymeric molecules. Because many polymers, including proteins, are amphoteric, it is understood that a particular molecule may serve as either cationic polymer or an anionic polymer, depending on the reactions conditions. In another embodiment of the invention, it is understood that both the cationic polymer and the anionic polymers may be the same polymeric molecule, wherein one population of the molecule maintains a net positive charge and a second population of the molecule maintains a net negative charge under the conditions of coacervation. (e.g. by controlling pH conditions of the starting solutions).

In another embodiment of the invention, it is understood that more than one cationic-polymeric molecule and/or more than one anionic-polymeric molecule may be employed in the coacervation process to form microparticles. It is understood that the different cationic-polymeric molecules (or the different anionic polymeric molecules) may be employed in the coacervation process as a cationic-polymeric mixture (or anionic-polymeric mixture) or they may be added separately to the coacervation reaction mixture.

For certain therapeutic applications of the microparticles, preferred cationic and anionic polymers are biodegradable and biocompatible. "Biodegradable," as used herein, means that the composition will degrade or erode in vivo to form smaller chemical species. Degradation can result, for example, by enzymatic, chemical and physical processes. For applications of the microparticles as bioreagents, polymers that are not readily susceptible to degradation in vivo or in vitro may be preferred.

Cationic and anionic polymers of the invention preferably have a molecular weight range of about 12,500 Daltons to about 1,000,000 Daltons, more preferably about 25,000 Daltons to about 500,000 Daltons, even more preferably about 35,000 Daltons to about 300,000 Daltons, and most preferably about 35,000 Daltons to about 150,000 Daltons. Polymers that are polypeptides will preferably have a length that is greater than about ninety amino acid residues.

Cationic polymers will comprise a net cationic charge, and anionic polymers will comprise a net anionic charge. A "net cationic charge," as defined herein, means the positive numerical value obtained when the total number of strongly negative charges is subtracted from the total number of strongly positive charges, using the below described parameters in counting strongly positive or strongly negative charges. Conversely, a "net anionic charge," as defined herein, means the positive numerical value obtained when the total number of strongly positive charges is subtracted from the total number of strongly negative charges, using the following parameters in counting strongly positive or strongly negative charges. In accordance with the relevant parameters for determining cationic or anionic charge, lysine free amino residues are counted as 1; arginine residues are counted as 2; other strongly positive charges (e.g. metals bound to carbon), are counted according to their valence number; strongly negative charges (e.g. sulfate ($-2$ valence), nitrate ($-1$ valence), phosphate ($-1$ valence), or other strong acid groups) are counted according to their valence number; acetic acid carboxylate groups (e.g. glutamate and aspartate) are not considered as strong negative charges; groups such as R—CYX—COO$^-$, wherein X is selected from the group consisting of halogen and other electron withdrawing group and Y is selected from the group consisting of hydrogen, halogen and other electron withdrawing groups, or wherein both X and Y are replaced by a multivalent electron withdrawing group (e.g.=O), are considered strongly negative charges. Preferred cationic polymers of the invention have a ratio of net cationic charge/Dalton of molecular weight polymer that is about 0.0001 to 0.6, more preferably about 0.001 to 0.5, and most preferably about 0.05 to about 0.4. Preferred anionic polymers of the invention have a ratio of net anionic charge/Dalton of molecular weight of polymer that is about 0.0004 to 0.16, more preferably about 0.0001 to 0.08, and most preferably about 0.001 to about 0.01.

Examples of cationic polymers include the following:
Alkaline phosphatase
Amylase
Insulin
DNAse
Erythropoietin
Fibrin
Fibrinogen
Fibromodulin
Globulin, various
Interferon
Kallikrein
Lactalbumin
Lactate dehydrogenase
Lactogen
Lactoglobulin
Leucine aminopeptidase
Lipase
Lipoprotiens
Luciferase
Lysozyme
Myoglobin
Myokinase
Papain
Peroxidase
Polygalacturonase
Polyarginine
Poly-epsilon-CBZ-L-lysine, CAS 25931-47-9
Poly-delta-CBZ-ornithine, CAS 118578-06-6
Poly-lysine
Poly acids would include those with random incorporation of lysine and arginine in the chain. Presence of other amino acid residues will not interfere.
Pyruvate kinase
RNAse
Streptokinase Thrombin Preferred cationic polymers of the invention are gelatin and albumin.

Examples of anionic polymers include the following:
Fluoroacetylated proteins, carbohydrate or other polymer.
Dextran sulfate
Poly-A, Poly-C, Poly-G, Poly-I, Poly-T, Poly-U, or combinations of these
Polygalacturonic acid
Polyacids may be d, l, or any mixture
Poly(mono or difluoro)glutamic acid
Poly(mon or difluoro)homologues to above
Polylactic acid
Poly lactide/glycolide
Sulfated proteins
Sulfated carbohydrates
Sulfated inulin
Sulfated agarose
DNA
RNAsense/antisense Preferred anionic polymers of the invention are chondroitin sulfate A and chondroitin sulfate C.

Factors to be considered in selecting anionic and cationic polymers and in choosing the optimal molecular weight for such polymers include, for example, the desired polymer degradation rate, mechanical strength of the polymers, and the rate of dissolution of the polymer in aqueous media. One consideration in the design or selection of polymer that comprises a protein is the presence or absence of protease recognition sequences. For example, several three-amino acid or four amino acid protease recognition sequences are known in the art. These sequences may be naturally present in a particular protein or they may be engineered into (or deleted from) naturally occurring proteins using various techniques known in the art including, for example, genetic engineering techniques and in vitro peptide synthesis techniques.

As indicated above, in one aspect, the invention relates to the incorporation of a specific binding component in a matrix of microparticles formed by the process of coacervation. The binding component can be any molecule capable of binding another molecule and which can become entangled with the cationic and anionic polymers of the microparticle and still maintain the ability to bind with its binding ligand. In a preferred embodiment, the binding molecule will be a member of a specific binding pair. The binding component may be added to the coacervation reaction mixture and become physically entangled with the cationic polymer and anionic polymer during the coacervation process. The binding component may be covalently bonded to one or both of the polymers and thus become entangled with the polymers during the coacervation process. The binding component may be covalently bonded to carrier molecule that is added to the reaction mixture during the coacervation process and thus become entangled with the polymers via the entanglement of the carrier molecule with the polymers during the coacervation process. Binding components may be attached to the carrier molecules or the anionic or cationic polymer with various spacer/linker molecules, preferably organic spacers that range in length from C2 to C24.

Specific binding pairs may include immunological pairs such as antigen antibody pairs, biotin-avidin, hormones-hormone receptors, cellular receptors toxins and other ligand molecules that are known to bind to cellular receptors (e.g. snake toxins, toxin II, toxin A, spider toxins, cholera toxin, pertussis toxin, botulinum toxin, saxitoxin, oligomycins), nucleic acid duplexes, IgG-protein A, and polynucleotide pairs such as DNA-DNA, DNA-RNA, RNA-RNA, and RNA-RNA. It is contemplated as part of this invention that, for all of the specific binding reagents discussed herein, derivatives of those reagents may also be employed. For example, for antibody reagents as members of specific binding pairs, antibodies may comprise chimeric antibodies, single chain antibodies, Fab fragments and the like.

In a preferred embodiment of the invention the binding component is an avidin-type molecule. As used herein, an "avidin-type molecule" refers to the native egg-white glycoprotein avidin, to deglycosylated forms of avidin, to bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin and Neutralite Avidin. The invention also relates to monomeric and multimeric avidins and streptavidins, including, for example, monomeric, dimeric, trimeric, tetrameric, pentameric etc. forms of avidins or streptavidins, or derivatives thereof. Avidin-type molecules are commercially available and they can be prepared by techniques well known in the art (Green, 1990, *Methods Enzymol.* 184:51; Hiller et al., 1990, *Methods Enzymol.* 184:68; Bayer et al., 1990, *Methods Enzymol.* 184:80; Bayer et al., 1990, *Methods Enzymol.* 184:138). Recombinant avidin and streptavidin can be prepared by standard recombinant DNA techniques, for example, as described by Chandra and Gray, (1990, *Methods Enzymol.* 184:70) for recombinant avidin and by Argarana et al. (1986, *Nucl. Acids Res.* 14:1871) for recombinant streptavidin.

One unit of avidin activity is defined as the amount of protein that will bind 1 mg of d-biotin (4-hydroxyazobenzene-2'-carboxylic acid; HABA) (Biochem. J.; 89, 599 (1963)). Highly purified avidin or streptavidin typically has a specific activity of about 4-14 units/mg. Preferably, preparations of avidin type molecules with a specific activity of about 9 U/mg, more preferably about 11 U/mg are employed to form the microparticles of the invention.

In another preferred embodiment of the invention, the binding component is a biotin type molecule. As used herein, "a biotin type molecule" refers to biotin (4-hydroxyazobenzene-2'-carboxylic acid; HABA) or any analog or derivative thereof which binds specifically with an avidin-type molecule as defined herein. In preferred embodiments, the binding component is natural biotin, which is coupled to a carrier molecule or to an anionic or cationic polymer through an amide bond, preferably via linker a molecule with the approximate size of a seven carbon chain. In some examples it may be advantageous to have a biotin derivative that does not bind as tightly as natural biotin, or a biotin derivative that binds to chemically modified, or genetically mutated, avidin or streptavidin in preference to natural biotin. Examples of such biotins are norbiotin, homobiotin, oxybiotin, iminobiotin, desthiobiotin, diaminobiotin, biotin sulfoxide, and biotin sulfone. Other modifications of biotin, including further modification of the above examples are also included. Biotin may be conjugated to proteins via primary amines (i.e., lysines).

In one example, biotin is conjugated to carrier molecule, wherein the carrier molecule comprises a polymer (e.g. a protein or other polymer) with a molecular weight of from about 20,000 Daltons to about 500,000 Daltons. In another example, biotin is conjugated to the anionic polymer or the cationic polymer or both. For example, biotinylation of gelatin or other polymer or carrier molecule, will preferably result in biotinylated polymers that comprise biotin in the amount of from about 0.01 mole percent to about 15 mole percent, more preferably from about 0.1 mole percent to 10 mole percent, most preferably about 0.5 mole percent to about 8 mole percent.

In preparing coacervates of the present invention, a solution of the cationic polymer is brought into contact with a solution of the cationic polymer. The concentration of cationic polymer and anionic polymer in the reagent solutions and in the reaction mixture can vary substantially depending on the polymers employed and the desired size of the microparticles. As one example, mixing can be conveniently carried out by using equal volumes of an aqueous solution of gelatin or other cationic polymer and an aqueous solution of chondroitin sulfate or other anionic polymer solution. The reaction mixture preferably contains a concentration of gelatin or other cationic polymer of about 0.05% to about 10% and a concentration of chondroitin sulfate or other anionic polymer of about 0.05% to about 10%.

The temperature to be employed in forming coacervates may vary somewhat with the particular method and components employed. Thus, a temperature from about −8° C. to about 70° C. can normally be used. In a preferred embodiment of the invention, the cationic polymer solution ranges in temperature from about room temperature to about 60° C. The anionic polymer is kept on ice and the cationic polymer is added to the anionic mixture slowly, with rapid stirring. The volume of the anionic polymer solution is preferably 4 to 5 times that of the cationic polymer and the final reaction temperature is near 0° C.

The pH to be employed in forming the coacervate microparticles can also vary over a fairly wide range. The pH of the both starting anionic and cationic polymer solutions, and of the coacervation mixture, may be varied depending on the polymers employed and the desired yield and size of the coacervate microparticles. When gelatin and chondroitin sulfate polymeric components are employed, the pH of the gelatin solution predominates over that of the chondroitin solution in determining the pH of the mixed solution of the two, and optimum results in terms of both the size and yield of coacervate microparticles particles are obtained at a pH of about 2.5 to about 5.0.

It is within the skill of one of ordinary skill in the art to vary the reaction conditions in terms of pH, temperature, component concentrations, and mixing conditions to optimize conditions for yield and/or a desired particle size. The binding component can be added to either the solution containing gelatin or other cationic polymer or the solution containing chondroitin sulfate or other anionic polymer. When an avidin-type molecule is employed as the binding component, the binding component is preferably added to the solution containing gelatin or other cationic polymer.

After the formation of microparticles in the coacervation reaction mixture the microparticles may be stabilized by the addition of a cross-linking agent to the reaction mixture. Alternatively, the microparticles may be isolated from the reaction mixture and then crosslinked immediately in a crosslinking reaction mixture or stored for crosslinking at a later date. In one embodiment, the microparticles are isolated from the reaction mixture, dried for storage, and crosslinked at a later date. Cross-linking is particularly useful for protein based microparticles but may not be necessary step for certain carbohydrate based microparticles such as, for example, those made using chitosan. Cross-linking reagents that may be employed include glutaraldehyde and other dialdehydes, including aromatic and aryl dialdehydes, trialdehydes, organosulfur crosslinking reagents, carbodiimides such as EDC (1-ethyl-3-(3-dimethylaminopropyl)-carbodiimide, DCC (N,N'-dicyclohexylcarbodiimide), carboxyls (peptide bond) linkage, DSS (Disuccinimidyl suberate), SPDP (N-succinimidyl 3-[2-pyridyldithio]propionate) bis(sulfosuccinimidyl) suberate, dimethylsuberimidate, etc. For example, the reaction mixture may be adjusted to contain from about 0.01% to about 0.8%, preferably about 0.1% to about 0.3% glutaraldehyde. The degree of cross-linking of the microparticles will affect the rate of degradation of the microparticles in vivo. Thus one of skill in the art may optimize the degree of cross-linking to achieve a desired therapeutic agent release profile from the microparticles. After completion of the crosslinking reaction, the microparticles are recovered from the reaction medium by conventional means such as, for example, decantation, filtration, or centrifugation.

As discussed above, size of the particles is affected by temperature and pH of the coacervation reaction and by component concentration in the coacervation reaction mixture. Particles may also be size fractionated using techniques that are known in the art such as, for example, by sucrose gradient centrifugation or elutriation. The optimal size of the microparticles will depend on the intended use of the microparticles, including the intended mode of administration and the desired release profile of the therapeutic agent. Particle size may be reduced by techniques known to those skilled in the art such as grinding or milling.

Some general considerations on particle size are as follows. When microparticles are intended for intravenous injection, their size is to be small enough to permit them to pass through capillary beds, e.g., less than about 5 microns in diameter. When microparticles are intended for inhalation, their size is also preferably to be less than about 5 microns, and those intended to reach deep alveolar sites are preferably to be less than about 2 microns. For uptake of particles by Peyer's patches, particles of less than about 10 microns, and preferably about 5 microns in diameter are preferred. A particle size range of about 0.1 to 10 microns encompasses the size range of particles that are respirable, that will travel to the alveoli, as well as the size range of particles that are taken up by the gut associated lymphatic tissue.

Typically, the microparticles will comprise a weight ratio of binding component to total particle weight of about 0.01% (w/w) to about 50% (w/w), preferably about 0.1% (w/w) to about 30% (w/w), and more preferably about 0.5% (w/w) to about 20% (w/w). In preferred embodiments of the invention, a significant portion of the binding component that is bound to the microparticle is bound to the interior portion of the microparticle. For example, preferably at least 5%, 10%, 15%, 20%, 25%, or 30% of the bound binding component is contained within the interior volume of the microparticles.

The microparticles of the invention are useful for the sustained release of therapeutic agents. As used herein, "sustained release" refers to the release of a therapeutic agent from the coacervate microparticle that occurs over a period that is longer than the period during which a biologically significant amount of the therapeutic agent would be available following direct administration of a solution of the therapeutic agent. It is preferred that a sustained release be a release of a therapeutic agent that occurs over a period of greater than two days. The sustained release of the therapeutic agent from the coacervate microparticles can be a continuous or a discontinuous release, with relatively constant or with varying rates of release. The continuity of release and level of release can be affected by the type of cationic and anionic polymers used to form the coacervate microparticles, the degree of cross-linking of the coacervate microparticles, the level of loading of the therapeutic agent in the microparticles, and the selection of particle coatings or excipients employed in microparticle formulations.

The term "therapeutic agent," as used herein, relates to any agent having a biological effect. Thus, the term includes, by way of example, and not by limitation, compounds useful for the treatment or prevention of disease, for obtaining a cosmetic enhancement, or for obtaining pain relief. Therapeutic agents of the invention may be of any nature including for example, small molecule organic compounds, biological macromolecules, polypeptides, nucleic acid molecules, snake toxins, spider toxins, botulinum toxin, pertussis toxin, cholera toxin, virus particles, or metal ions. It is contemplated as part of the invention that more than one therapeutic agent may delivered as part of the same microparticle. The second therapeutic agent may be specifically bound to the same binding component or a different binding component as the first therapeutic agent, or it may be bound nonspecifically to the microparticles. For example, it is contemplated as one aspect of the invention that therapeutic nucleic acids may be incorporated into the microparticles, preferably via incorporation as part of the coacervation process.

Therapeutic agents are attached to microparticles via a specific binding interaction, either directly or indirectly, with the binding component in the microparticles. Preferably, the therapeutic agent is attached to the microparticles indirectly, via a linking moiety, wherein the linking moiety specifically binds to the binding component. A preferred linking moiety is a biotin type molecule, as defined herein. Another preferred linking moiety is an avidin type molecule, as defined herein. Linking moieties are preferably covalently attached to the therapeutic agent. Linking moieties may be attached to the therapeutic agent with a linker/spacer molecule, preferably an organic spacer that ranges in length from C2 to C24.

Typically, the microparticles will comprise a weight ratio of therapeutic agent to total particle weight of about 0.01% (w/w) to about 50% (w/w), preferably about 0.1% (w/w) to about 30% (w/w), and more preferably about 0.5% (w/w) to about 20% (w/w). The amount of therapeutic agent used will vary depending upon the desired effect of the agent, the planned release levels, and the time span over which the agent will be released.

Microparticles are loaded with therapeutic agent by contacting the microparticles with solvent containing the therapeutic agent. The solvent may be any medium that solubilizes the therapeutic agent so that solvent containing solubilized therapeutic agent is able to permeate the matrix of the microparticles and allow for the specific binding of the therapeutic agent with the binding component. In a preferred embodiment of the invention, the solvent is aqueous medium and the microparticles are loaded with the therapeutic agent by soaking the particles in the aqueous medium containing the therapeutic agent. Microparticles may be loaded with therapeutic agent at or near the time of administration or they may be loaded with therapeutic agent and then stored in wet or dry form for later administration.

In preferred embodiments of the invention the, a significant portion of the therapeutic agent that is bound to the microparticle is bound to the interior portion of the microparticle. For example, preferably at least 5%, 10%, 15%, 20%, 25%, or 30% of the bound therapeutic agent is bound within the interior volume of the microparticles.

In one embodiment of the invention, targeting molecules are attached to the surface of the microparticles. Targeting molecules, as used herein, refers to any molecules that bind to specific types of cells or extracellular components in the body. For example, targeting molecules which bind to cellular receptors can be employed to direct the pharmaceutical compositions toward particular cells types. Examples of targeting molecules that can be used to target particular cell types are hormones, antibodies, cell adhesion molecules, saccharides, drugs, and neurotransmitters. Targeting molecules may be attached to the microparticles directly or via linkers. If the cationic polymer is a protein such as, for example, gelatin or albumin, for example, targeting molecules may be attached directly to the surface of the microparticles as part of the crosslinking step for microparticle stabilization as described above.

In general, the range of possible targets is dependent on the route of administration of the microparticles. For systemic injections, the specificity of this delivery system is affected by the accessibility of the target to blood borne microparticles, which in turn, is affected by the size range of the particles. For subcutaneous injections, the targetable cells include, for example, cells that reside in the connective tissue (e.g. fibroblasts, mast cells, etc.), Langerhans cells, keratinocytes, and muscle cells. For intrathecal injections, the targetable cells include, for example, neurons, glial cells, astrocytes, and blood-brain barrier endothelial cells. For intraperitoneal injection, the targetable cells include, for example, the macrophages and neutrophils.

In one embodiment of the invention, the polymeric molecules, or particles formed therefrom, may be modified by the addition of polyoxyethylene or polyoxypropylene groups to available functional groups on the polymers, the therapeutic agents, the binding component or the linking moiety, or other protein incorporated into the microparticle.

Microparticles of the invention may comprise coatings or other excipients to enhance or alter the therapeutic agent release profile or to protect the microparticles or therapeutic agents from degradation before they are delivered to a target site. For example, microparticles may comprise enteric coatings. Enteric coatings allow the therapeutic agent delivery system to pass through the stomach intact and dissolve upon reaching the intestine. For example, aqueous-based suspensions such as Eudragit® L30D-55 (Rohm Tech) and Kollicoat® MAE 30 DP (BASF) or coating materials supplied as powders like Eudragit® L100 or AQOAT® AS (Shin-Etsu) are used to protect microparticles from the low pH of the stomach. Upon reaching the near-neutral pH of the small intestine, these coatings dissolve rapidly. Enteric coats may be applied to microparticles or to compressed tablets containing microparticles.

Microparticles may also comprise sustained release coatings. These coatings allow for gradual release of a drug substance through the protective barrier. The oldest of these sustained release coating materials, shellac, no longer commonly used because of quality control problems associated with naturally occurring excipients. Two types of commonly employed sustained release coatings are ethylcellulose-based Aquacoat® (FMC) and Surelease® (Colorcon) or the acrylic-based Eudragit® NE and RS lines (Rohm Tech) and Kollicoat® SR 30D (BASE). Sustained-release coatings have a variety of drug delivery capabilities. When used as an external coating, ethylcellulose coatings allow a gradual zero-order release of the drug substance. Acrylic-based systems, on the other hand, produce a more sigmoidal dissolution profile, delaying drug release based on the thickness of the coating, with a relatively rapid release thereafter. This delay has been attributed to the solubility of the drug substance or hydration of the barrier. Sustained-release coatings typically require process-aiding excipients such as plasticizers and anti-tacking agents in their formulations. An exception is the Surelease system, which is diluted with purified water before application. Sustained-release coating permeability can be enhanced with water-soluble excipients such as HPMC for the ethylcellulose systems or water-insoluble, but freely permeable, Eudragit® RL 30D (Rohm Tech) in the acrylic systems. Such inclusions increase the types of sustained-release systems possible. Sustained release coatings may be applied to microparticles or to compressed tablets containing microparticles.

Microparticles of the invention may be administered orally or parenterally. Methods of parenteral delivery include, for example, topical, intra-arterial, intramuscular, subcutaneous, intramedullary, intrathecal, intraventricular, intravenous, intraperitoneal, or intranasal administration. Microparticles of the invention may be formulated in any art known vehicle. Such vehicles include, for example, those described in REMINGTON'S PHARMACEUTICAL SCIENCES, 16th Edition, 1980 and 17th Edition, 1985, both published by Mack Publishing Company, Easton, Pa., the disclosures of which are incorporated by reference herein in their entireties. Formulations of the microparticles of the invention may contain suitable pharmaceutically acceptable carriers comprising excipients and auxiliaries that facilitate processing of the microparticles. Formulations may also contain other active ingredients in addition to the microparticles or they may contain more than one type of therapeutic microparticle.

Microparticles for oral administration can be formulated using pharmaceutically acceptable carriers well known in the art in dosages suitable for oral administration. Such carriers enable the microparticles to be formulated as tablets, pills, draggers, capsules, liquids, gels, syrups, slurries, suspensions and the like, for ingestion by the patient. Commonly used excipients for the formation of oral dosage forms include, for example, carbohydrate or protein fillers such as sugars, including lactose, sucrose, manifold, or orbital; starch from corn, wheat, rice, potato, or other plants, cellulose such as methyl cellulose, hydroxypropylmethyl-cellulose, or sodium carboxymethylcellulose, and gums including arable and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Microparticles for injection may be formulated, for example, as an aqueous suspension of microparticles, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the microparticles may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents that increase the solubility of the compounds to allow for the preparation of highly concentrated solutions.

For topical or mucosal administration, penetrants appropriate to the particular barrier to be permeated are used in the formulation. Such penetrants are generally known in the art. For administration to the lungs, aerolization is the desired mode of administration. Any suitable, nebulizing device may be employed, most conveniently, a metered dose inhaler.

As one aspect of the invention, it is contemplated that the microparticle of the invention may be used in the treatment of cancer. Microparticles loaded with an anti-neoplastic agent can be injected or implanted into the cancerous site to provide for the sustained release of the anti-neoplastic agent. In one application, loaded microparticles are left at the site of a tumor after surgical removal of the tumor.

In a further aspect of the invention, it is contemplated that microparticles that have been injected or implanted into a subject may be reloaded with therapeutic agent in situ by infusion of the therapeutic agent, preferably conjugated to a linking moiety, into the site containing the microparticles. For example, infusion may occur via intravenous injection of the therapeutic agent or via an infusion port at a particular site, i.e. a tumor site.

In a further aspect of the invention it is contemplated that microparticles of the invention may be employed for the delivery of, for example, antibacterial agents, anti-viral agents, anti-fungal agents, hormonal agents, contraceptive agents, anti-thrombolytic agents, anti-arthritic agents, anti-inflammatory agents, anti depression agents, and anti-psychotic agents, etc.

Having now generally described the invention, the same will be more readily understood through reference to the following examples, which are provided by way of illustration and are not intended to be limiting of the present invention unless specified.

EXAMPLE 1

Formation and Assessment of Coacervate Microparticles Containing Avidin

Seven mg of avidin is dissolved in 1 ml of sterile water and then mixed with 6 ml of 1% gelatin solution having a pH of 2.5. The mixture is heated to about 50° C. without the formation of a cloud. The 7 ml of the mixture is then flowed into 12 ml of a 2% chondroitin sulfate solution, pH 2.5. The mixture is diluted to 50 ml and crosslinking is effected by the addition of 660 µl of an 8% solution of glutaraldehyde and incubation of the mixture for fifteen minutes on ice. Coacervate microparticles are pelleted by centrifugation for 15 minutes at 2500 rpm, and then resuspended in 5-10 ml of sterile water, and the volume of suspension is adjusted to 50 ml with absolute ethanol. The coacervate microparticles are again pelleted by centrifugation as described above and the pellet is suspended in 5 ml absolute ethanol and set aside to dry overnight.

The next day, a sample of the dried coacervate microparticles is suspended in 1 ml of sterile water and vortexed for 30 seconds to remove unbound starting materials. After vortexing, the sample of coacervate microparticles is pelleted by centrifugation at 12,000 rpm and the pellet is resuspended in 200 µl antibody solution (phosphate buffered saline, pH 7.4-7.8). The 200 µl solution is divided into a reaction tube and a control tube. A 5 µl aliquot of a 5 mg/ml solution of biotin/horseradish peroxidase conjugate is added to the reaction tube. After 30 minutes, the microparticle suspension in the reaction tube is diluted to 1 ml with phosphate buffered saline, and then the microparticles are pelleted by centrifugation. The microparticles are resuspended in phosphate buffered saline and pelleted by centrifugation three additional times to remove unbound biotin/horseradish peroxidase. After the fourth centrifugation step, the microparticles are resuspended in 100 µl of phosphate buffered saline. A 1 ml aliquot of horseradish-peroxidase (HRP) substrate mix (Vector HRP) is added to both the resuspended microparticles and the microparticles in the control tube, and to a third tube containing 100 µl and 5 µl of biotin conjugated horseradish peroxidase. The third tube containing the biotin/HRP conjugate immediately turns dark purple upon the addition of HRP substrate. The control tube exhibits no color change, and the tube containing microparticles that had been reacted with the biotin/HRP conjugate immediately turns light purple and then darkens over several minutes. Microscopic examination of these particles shows that most microparticles are a dark purple, indicating that avidin is incorporated into the particles and that the avidin is able to bind substantial quantities of the biotin-HRP conjugate.

The formation of coacervate microparticles is described in U.S. Pat. Nos. 5,759,582; 5,972,707; 6,207,195; 6,410,517, and these patents are specifically incorporated herein by reference.

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A composition comprising microparticles having a matrix structure, wherein the matrix structure comprises the reaction product of at least one cationic polymer, at least one anionic polymer, and a binding component, wherein the binding component is distributed throughout the matrix structure of the microparticle, wherein the binding component is one member of a specific binding pair comprising the binding component and a linking moiety, wherein the linking moiety is suitable for linkage with a variety of therapeutic agents; and wherein the composition further comprises a therapeutic agent, wherein the therapeutic agent is linked to the linking moiety, and the therapeutic agent is bound to the microparticles through the specific interaction of the linking moiety with the binding component.

2. The composition of claim 1, wherein the therapeutic compound is bound to the interior matrix of the microparticle.

3. A composition of claim 1, wherein the linking moiety molecule is bound to the therapeutic agent by an organic spacer ranging in length from C2 to C24.

4. The composition of claim 1, wherein at least one cationic polymer is selected from the group consisting of gelatin and albumin and at least one anionic polymer is chondroitin sulfate.

5. The composition of claim 1, wherein the binding component is an avidin-type molecule and the linking moiety is a biotin-type molecule.

6. The composition of claim 1, wherein the binding component is a biotin-type molecule and the linking moiety is an avidin type molecule.

* * * * *